United States Patent
Duong et al.

(10) Patent No.: US 7,608,071 B2
(45) Date of Patent: *Oct. 27, 2009

(54) CRYOSURGICAL PROBE WITH ADJUSTABLE SLIDING APPARATUS

(75) Inventors: Thach Duong, Irvine, CA (US); Jay J. Eum, Irvine, CA (US)

(73) Assignee: Endocare, Inc., Irvine, CA (US)

( * ) Notice: Subject to any disclaimer, the term of this patent is extended or adjusted under 35 U.S.C. 154(b) by 51 days.

This patent is subject to a terminal disclaimer.

(21) Appl. No.: 11/857,095

(22) Filed: Sep. 18, 2007

(65) Prior Publication Data

US 2008/0009845 A1    Jan. 10, 2008

Related U.S. Application Data

(63) Continuation of application No. 11/685,058, filed on Mar. 12, 2007, now Pat. No. 7,381,207, which is a continuation of application No. 11/116,873, filed on Apr. 28, 2005, now Pat. No. 7,189,228, which is a continuation-in-part of application No. 10/603,883, filed on Jun. 25, 2003, now Pat. No. 7,207,985.

(51) Int. Cl.
   *A61B 18/02* (2006.01)
(52) U.S. Cl. .......................... 606/23; 606/22
(58) Field of Classification Search ............ 606/20–31; 607/88–92; 403/280–287, 289–305
See application file for complete search history.

(56) References Cited

U.S. PATENT DOCUMENTS

| | | |
|---|---|---|
| 3,524,446 A | 8/1970 | Crump |
| 3,800,552 A | 4/1974 | Sollami |
| 4,018,227 A | 4/1977 | Wallach |
| 4,206,760 A | 6/1980 | Davis |
| 4,258,888 A | 3/1981 | Sawn |
| 5,224,943 A | 7/1993 | Goddard |
| 5,254,116 A | 10/1993 | Baust |
| 5,452,582 A | 9/1995 | Longsworth |
| 5,520,682 A | 5/1996 | Baust |
| 5,800,487 A | 9/1998 | Mikus |
| 5,910,104 A | 6/1999 | Dobak |
| 5,978,697 A | 11/1999 | Maytal |
| 5,992,158 A | 11/1999 | Goddard |
| 6,039,730 A | 3/2000 | Rabin |
| 6,074,412 A | 6/2000 | Mikus |
| 6,106,517 A | 8/2000 | Zupkas |
| 6,306,129 B1 | 10/2001 | Little |

(Continued)

*Primary Examiner*—Ahmed M Farah
(74) *Attorney, Agent, or Firm*—Lawrence N. Ginsberg

(57) ABSTRACT

A cryosurgical probe assembly that includes a gas delivery assembly, including a stem and a fluid conduit subassembly bonded to the stem. The fluid conduit subassembly delivers and returns cooling fluid used for cryogenic cooling. The fluid conduit subassembly, comprises a shaft for providing a heat exchange surface for cryogenic ablation; a housing securely connected to said shaft; and, an insulation element slideably engaged with an inner surface of the shaft and slideably engaged with the stem. The cryosurgical probe assembly includes an adjustable sliding apparatus that includes a slider assembly securely attached to said insulation tube for slideably guiding the insulation tube along said shaft; and, a button assembly operatively connected to the slider assembly for allowing a user to actuate the slider assembly to provide a desired adjustment of the insulation tube relative to the shaft. A handle assembly is positioned about the housing.

9 Claims, 8 Drawing Sheets

U.S. PATENT DOCUMENTS

| | | |
|---|---|---|
| 6,547,785 B1 | 4/2003 | Heiner |
| 6,767,346 B2 | 7/2004 | Damasco |
| 6,936,045 B2 | 8/2005 | Yu |
| 7,160,291 B2 | 1/2007 | Damasco |
| 7,189,228 B2 * | 3/2007 | Eum et al. .................... 606/22 |
| 7,207,985 B2 * | 4/2007 | Duong et al. ................. 606/20 |
| 7,381,207 B2 * | 6/2008 | Duong et al. ................. 606/20 |
| 2002/0022832 A1 | 2/2002 | Mikus |
| 2002/0188287 A1 | 12/2002 | Zvuloni |

* cited by examiner

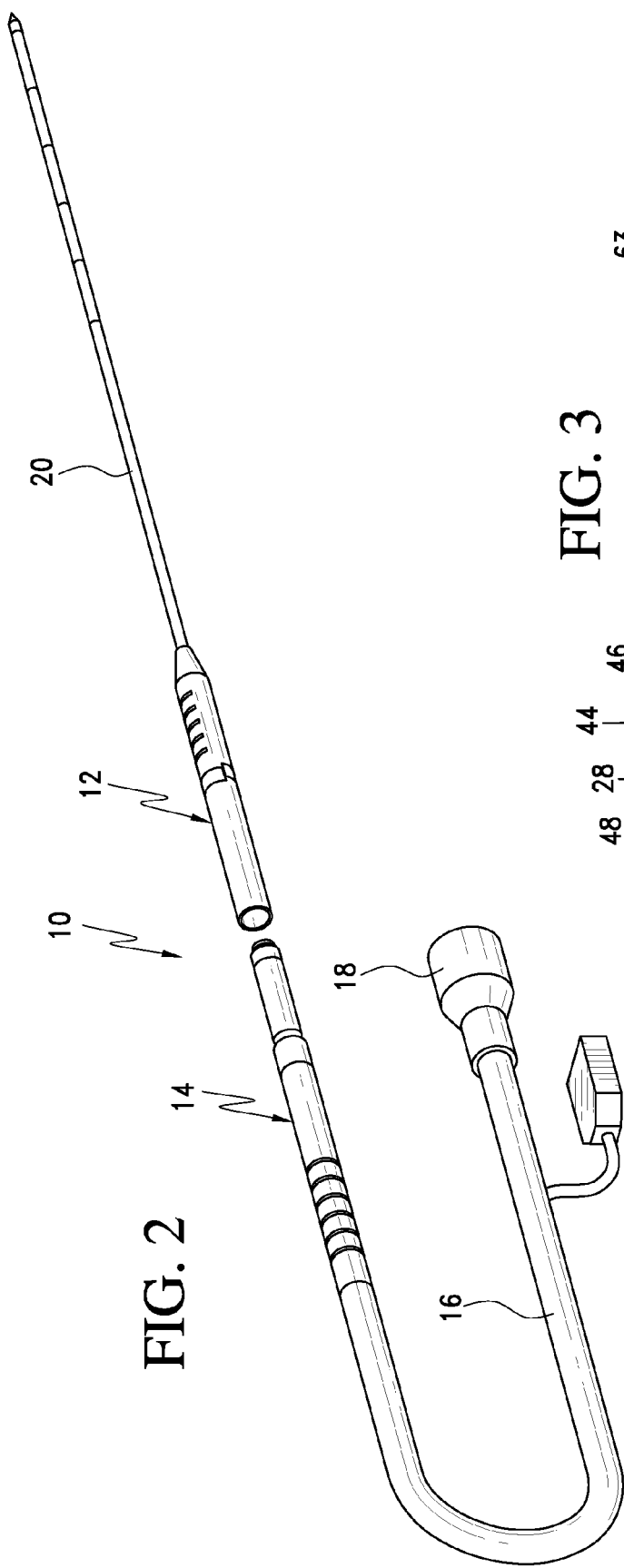
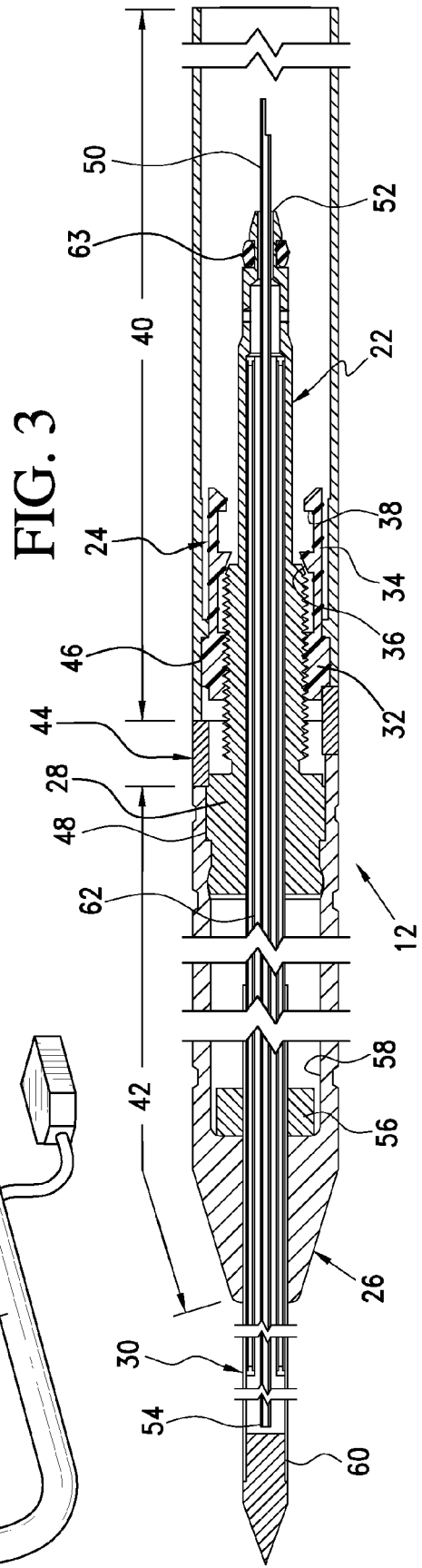

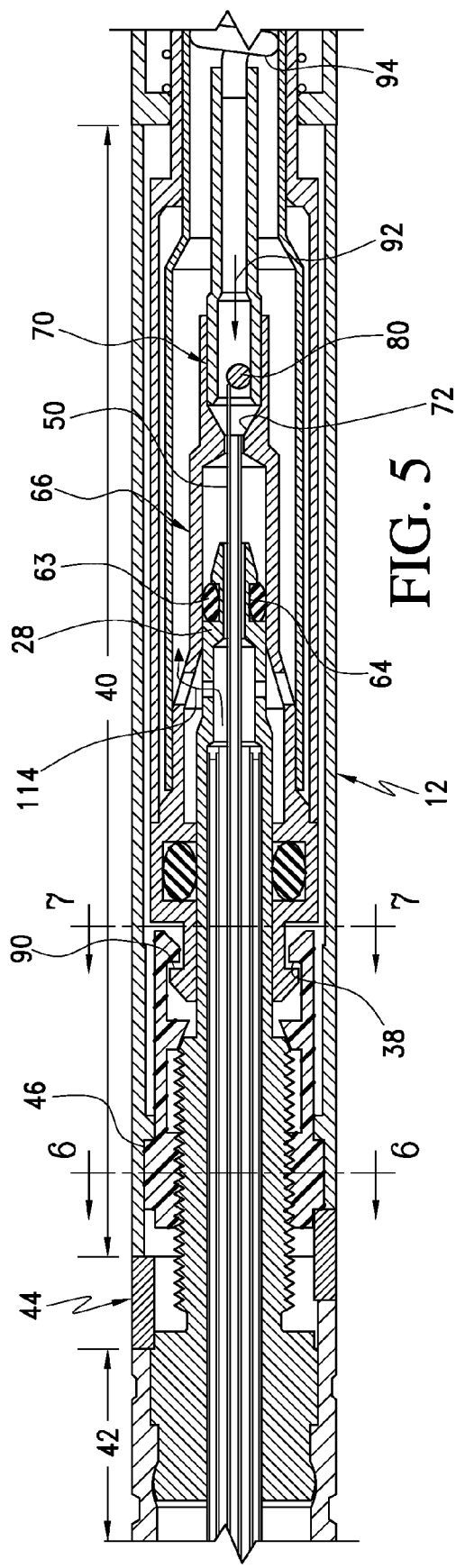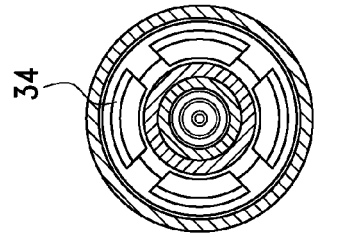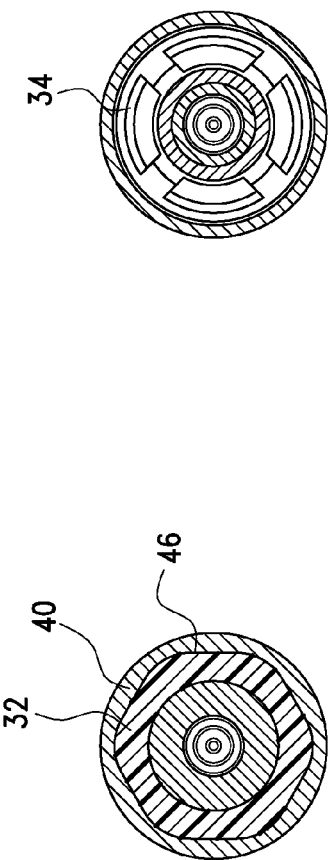

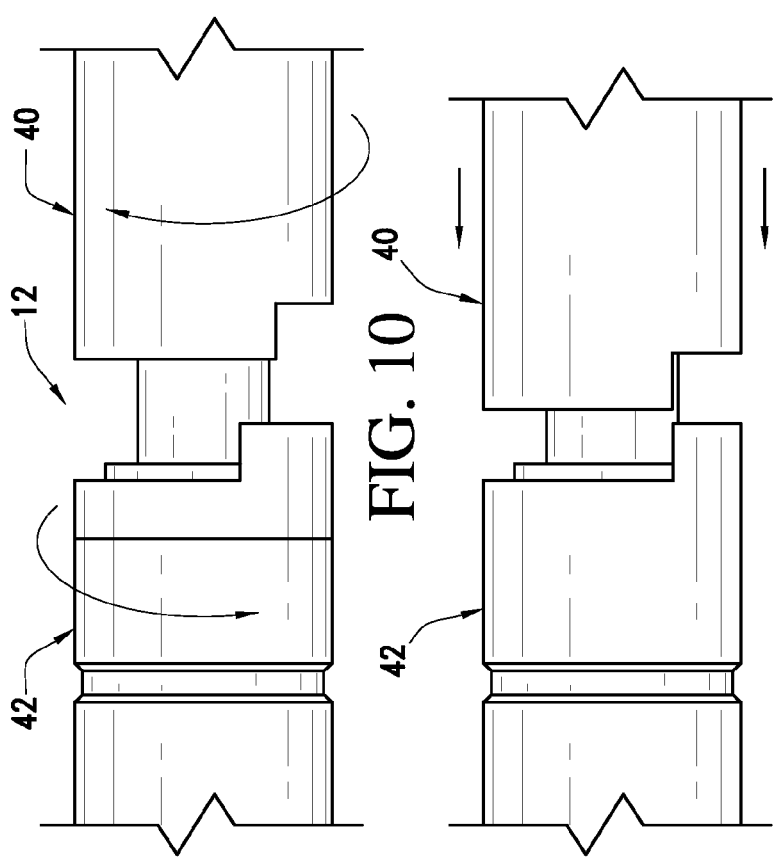
FIG. 10
FIG. 11
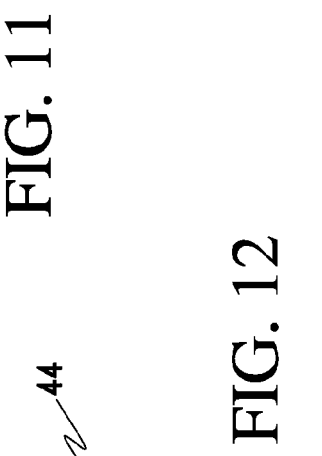
FIG. 12
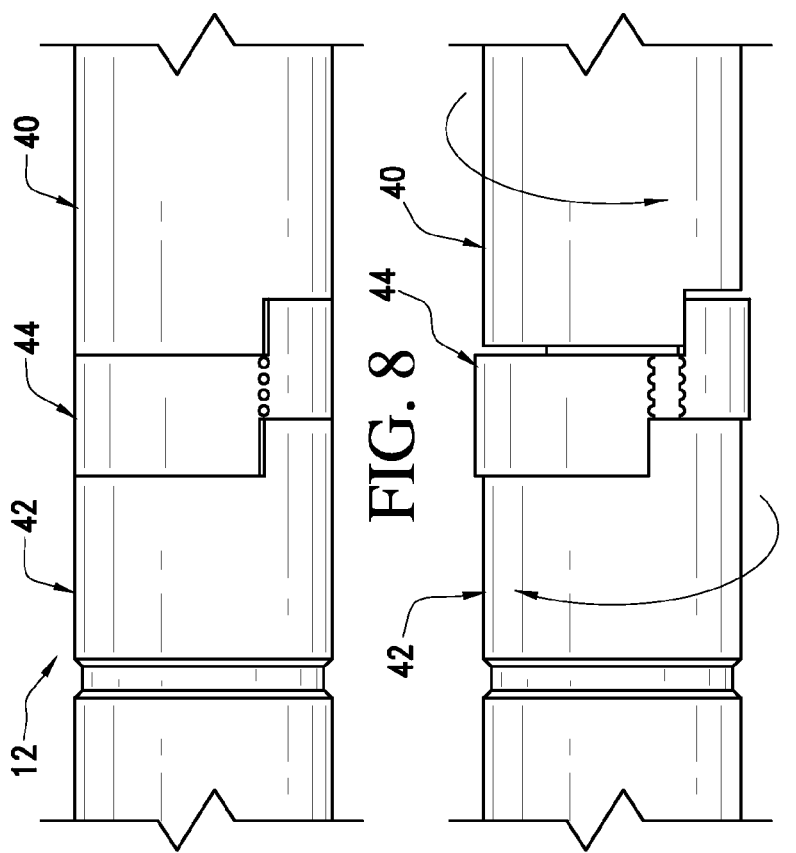
FIG. 8
FIG. 9

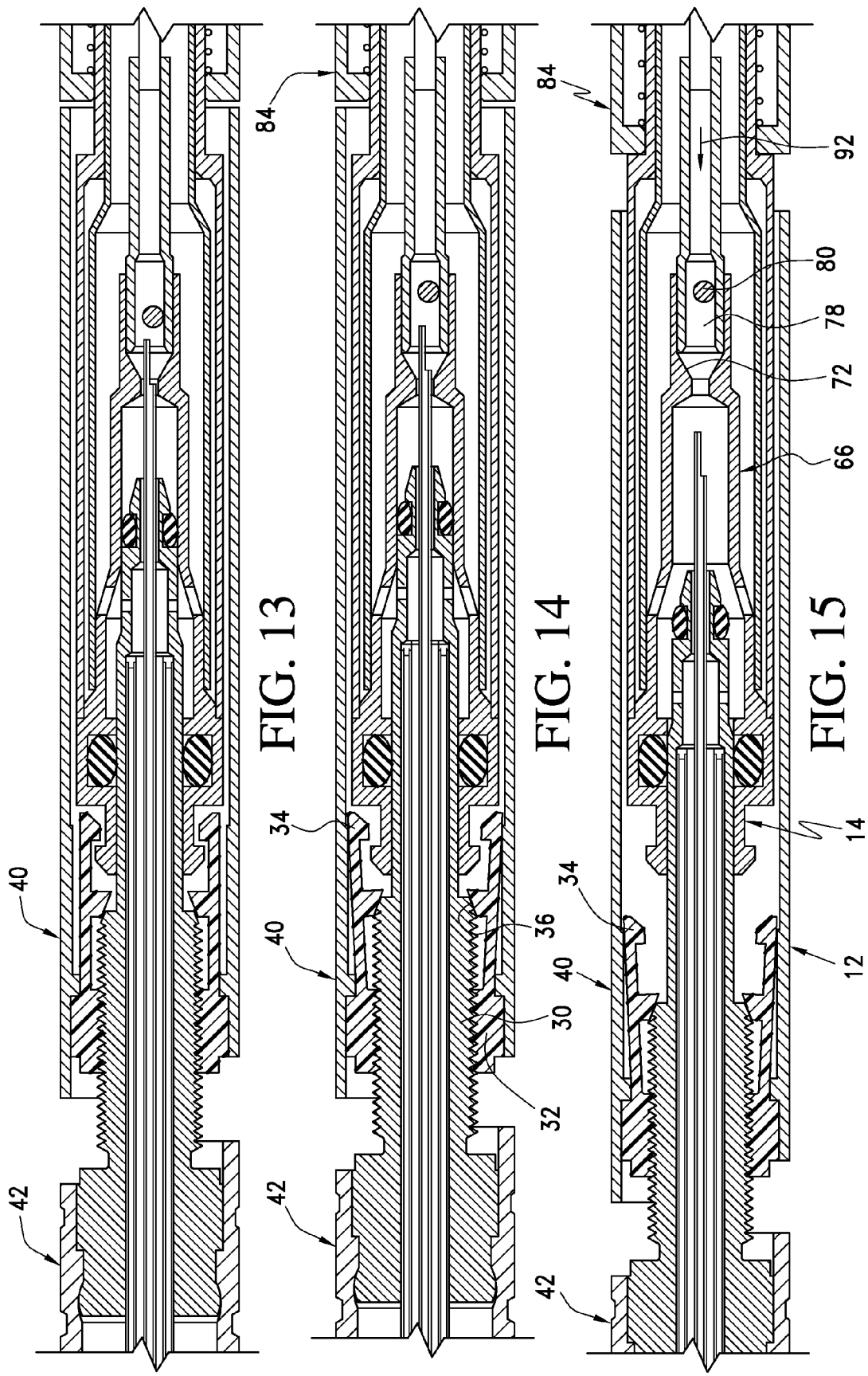

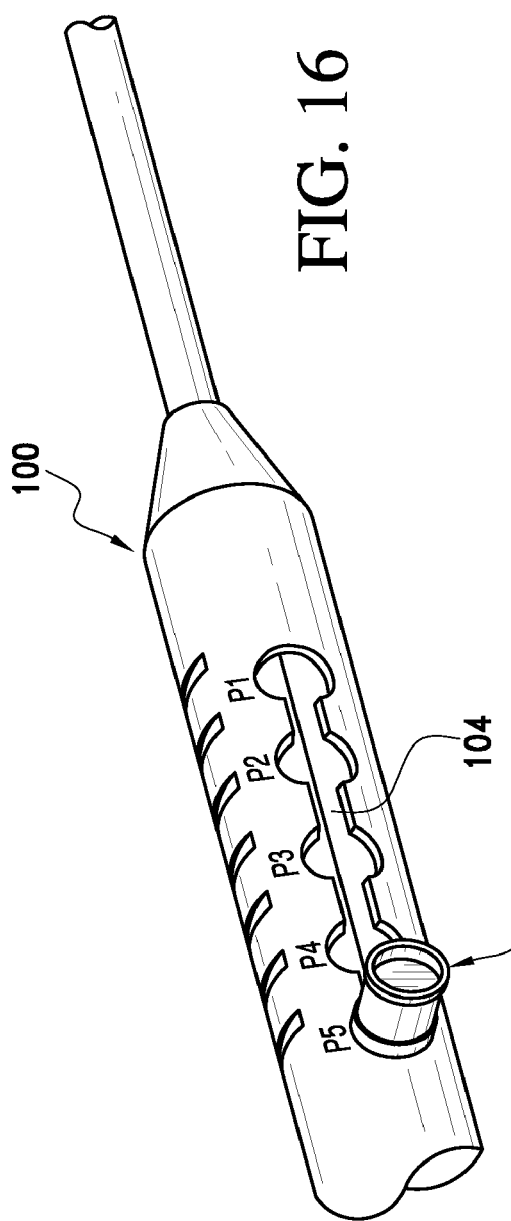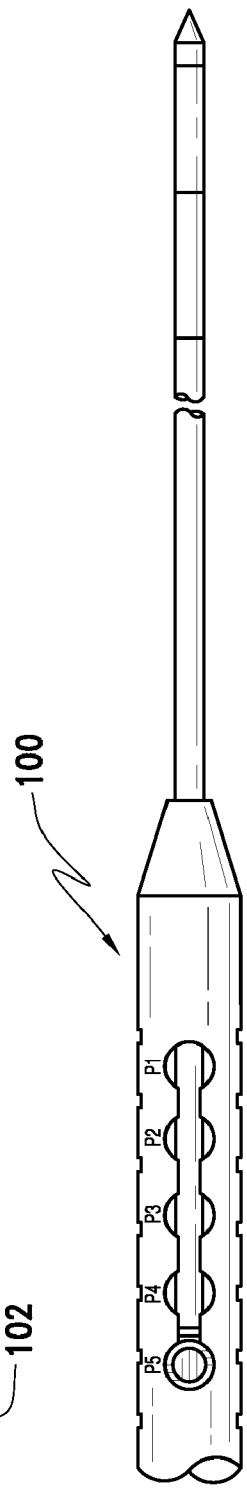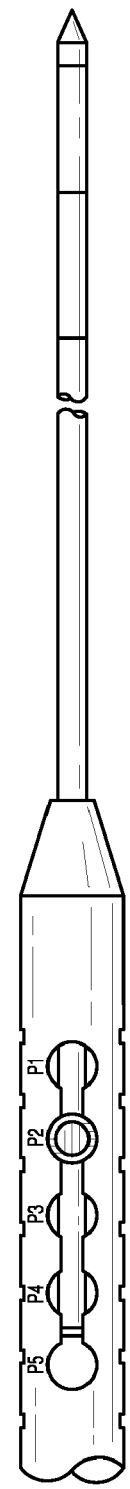

CRYOSURGICAL PROBE WITH ADJUSTABLE SLIDING APPARATUS

CROSS REFERENCE TO RELATED APPLICATIONS

This is a continuation of U.S. Ser. No. 11/685,058, entitled "Quick Disconnect Assembly Having a Finger Lock Assembly", filed on Mar. 12, 2007, which is a continuation of U.S. Ser. No. 11/116,873 (U.S. Pat. No. 7,189,228), entitled "Detachable Cryosurgical Probe with Breakaway Handle," filed Apr. 28, 2005 which is a continuation-in-part of U.S. Ser. No. 10/603,883 (U.S. Pat. No. 7,207,985), entitled "Detachable Cryosurgical Probe," filed Jun. 25, 2003. The entire disclosures of U.S. Ser. No. 11/685,058 and U.S. Ser. No. 11/116,873 are incorporated herein by reference for all purposes.

BACKGROUND OF THE INVENTION

1. Field of the Invention

The present invention relates to cryosurgical probes and more particularly to a cryosurgical probe with an adjustable sliding apparatus to adjust the size of the resulting iceball.

2. Description of the Related Art

Cryosurgery involving the use of a cryosurgical probe assemblies typically involves the use of cryoprobes that are each attached to a handle that are, in turn, connected to a high-pressure fluid line with a quick-disconnect for attachment to a fluid source. There is an inherent problem with this type of system inasmuch as each cryosurgical probe assembly should be used only once due to sterilization and performance factors. Therefore, typically, the entire cryosurgical probe assembly and high-pressure fluid line must be discarded after that single use. Due to these sterilization/performance requirements there is a need to assure that the cryosurgical probe assembly may be rendered non-useable after a single-use.

Previous attempts to mitigate this problem have involved utilizing a disposable sheath over a cryosurgical probe. For example, U.S. Pat. No. 5,910,104, issued to J. D. Doback, III et al, discloses a disposable, sterilizable sheath for use on a closed loop Joule-Thomson cryosurgical probe, and the combination of the disposable sheath and the closed loop probe. The sheath is slipped over the probe, thereby separating the probe from the environment. The sheath has a grip that fits over the handle of the cryosurgical probe. The sheath has a hollow multi-lumen catheter shaped and sized to fit snugly over the cannula of the cryosurgical probe.

U.S. Pat. No. 6,306,129 B1, issued to Little et al, also discloses the use of a disposable sheath over a cryosurgical probe.

Similarly, U.S. patent Publication US 2002/0022832 A1, to Mikus et al, discloses a cryoprobe assembly that includes a cryoprobe and an outer sheath assembly detachably connected thereto.

U.S. Pat. Publication US 2004/0267248 (U.S. Pat. No. 7,207,985), to Duong et al, entitled "Detachable Cryosurgical Probe", discloses a cryosurgical probe system that includes a fluid supply line connectable at an inlet section to a source of cryogenic fluid; a fluid connector assembly securely connected to an outlet section of the fluid supply line for receiving fluid from the outlet section of the fluid supply line; and, a detachable cryosurgical probe detachably connectable to the fluid connector assembly. The cryosurgical probe system includes the capability of providing return fluid flow.

U.S. patent publication US 2005/0010200 (U.S. Pat. No. 7,160,291), to Damasco et al, entitled "Detachable Cryosurgical Probe", discloses a cryosurgical probe system that includes a fluid supply line connectable at an inlet section to a source of cryogenic fluid; a fluid connector assembly securely connected to an outlet section of the fluid supply line for receiving fluid from the outlet section of the fluid supply line; and, a detachable cryosurgical probe detachably connectable to the fluid connector assembly. The fluid connector assembly includes a substantially cylindrical lock housing securely attached to the outlet section of the fluid supply line, the lock housing having a fluid inlet conduit for receiving high pressure fluid from the fluid supply line and a fluid outlet conduit for transferring return fluid from the cryosurgical probe to the fluid supply line. A locking mechanism is positioned at a locking portion of the lock housing to provide detachable engagement of a cryosurgical probe positioned therein. The detachable cryosurgical probe receives fluid from the fluid connector assembly and manipulates the fluid to provide suitable temperatures for cryosurgical treatment. It includes a fluid delivery/return manifold assembly having a fluid delivery section and a return manifold section. The return manifold section is positioned over a portion of the fluid delivery section. The return manifold section includes an insulative vacuum sleeve. The fluid delivery/return manifold assembly has a proximal end section. An outer sheath is securely positioned over the vacuum sleeve and extends from the fluid delivery/return manifold assembly. A lock anchor is securely positioned over the outer sheath. The lock anchor provides detachable connection to the fluid connector assembly of a detachable cryosurgical system. During operation fluid is delivered through the fluid delivery/return manifold assembly, through a Joule-Thomson (J-T) port defined at a distal end of the fluid delivery section and is returned through the return manifold section and delivered out of the cryosurgical probe. The insulative vacuum sleeve is provided between the outer sheath and the return manifold section at a control region of the outer sheath proximal to a distally located treatment region of the outer sheath. Unlike previous cryosurgical probe systems, the operative portion of the present system, i.e. the detachable cryosurgical probe, can be discarded after a single use. However, the fluid supply line and the connector assembly can be reused. The cryosurgical probe system includes the capability of providing return fluid flow. Suitable passageways in the detachable cryosurgical probe and the fluid connector assembly provide this feature.

U.S. Pat. No. 5,978,697, issued to Maytal, et al, discloses an MRI-guided cryosurgical system. The Maytal system includes: (a) an MRI magnet for accommodating a patient, the MRI magnet having at least one opening for enabling access of a surgeon to the patient, the MRI magnet including at least one channel extending therethrough for receiving a line member of a surgical device; (b) a surgical device, including: (i) an operating member for operating the patient; (ii) a control member for controlling the operating member, the control member being positioned externally to the MRI room; and, (iii) a line member having a first end connectable to the operating member and a second end connectable to said control member, wherein at least a portion of the line member is received within the channel of the MRI magnet.

SUMMARY OF THE INVENTION

In a broad aspect, the present invention is embodied as a detachable cryosurgical probe, including a disposable probe assembly, having a gas delivery assembly, comprising a stem and a fluid conduit subassembly bonded to the stem, the fluid conduit subassembly for delivering and returning cooling fluid used for cryogenic cooling. A finger lock element includes a distal finger lock element section having a threaded inner surface for engagement with a threaded outer surface of the stem; and, a plurality of radially spaced fingers extending proximally from the distal finger lock element section. Each finger has a ramped surface for operatively engaging an associated ramp section on the stem during use; and, a female lip at a proximal end thereof. A disposable handle assembly, includes: 1) a proximal handle section having a distal end having an inner surface that is operatively engaged with an outer surface of the finger lock element so as to resist relative rotation and axial motion therebetween; 2) a distal handle section having an inner surface that is operatively engaged with another outer surface of the stem so as to resist relative rotation and axial motion therebetween; and, 3) a breakaway collar positioned between the proximal handle section and the distal handle section.

A reusable probe assembly of the detachable cryosurgical probe, includes: a manifold assembly for receiving a cryogenic working fluid and transmitting the cryogenic working fluid to the gas delivery assembly. The manifold assembly includes a male lip at a distal end thereof; and, a reusable handle assembly secured about the periphery of the manifold assembly.

During operation, when the disposable probe assembly is attached, the breakaway collar is an integral unit which prevents relative rotation between the proximal handle section and the distal handle section. The female lip engages the male lip, thereby securing the reusable probe assembly to the disposable probe assembly. During an initial stage of detachment of the disposable probe assembly, the user rotates the proximal handle section in a first direction relative to the distal handle section to break away breakaway surfaces of the breakaway collar, allowing the breakaway collar to radially expand. During an intermediate stage of detachment of the disposable probe assembly the user counter rotates the proximal handle section in an opposite second direction relative to the distal handle section. The relative rotation between the proximal handle section and the distal handle section provides axial movement of the proximal handle section toward the distal handle section via the engagement of the threaded inner surface of the distal finger lock element section and the threaded outer surface of the stem, the axial movement being enabled by the radial expansion of the breakaway collar. The ramped surfaces of the radially spaced fingers engage the associated ramp section on the stem during the axial movement thereby urging the fingers to open. During a final stage of detachment the fingers open sufficiently to allow disengagement of the male lip from the female lip, thus enabling the disposable probe assembly to be detached from the reusable probe assembly.

Use of the finger lock element provides space savings relative to previous detachable mechanisms. The fingers extend in an axial direction along the cryoprobe. The cryoprobe has redundant safety features such as contacts for providing electrical confirmation of connections. The disposable probe assembly has a single use feature that prevents it from being reused without compromising its safety and performance.

A safety valve assembly is provided to minimize gas leakage and prevent "whipping" of the disposable probe assembly.

In one embodiment ice size and configuration can be modified as desired by selectively positioning a vacuum tube.

In another broad aspect the invention may be embodied as a cryosurgical probe assembly that includes a gas delivery assembly, comprising a stem and a fluid conduit subassembly bonded to the stem. The fluid conduit subassembly delivers and returns cooling fluid used for cryogenic cooling. The fluid conduit subassembly, comprises a shaft for providing a heat exchange surface for cryogenic ablation; a housing securely connected to said shaft; and, an insulation element slideably engaged with an inner surface of the shaft and slideably engaged with the stem. The cryosurgical probe assembly includes an adjustable sliding apparatus that includes a slider assembly securely attached to said insulation tube for slideably guiding the insulation tube along said shaft; and, a button assembly operatively connected to the slider assembly for allowing a user to actuate the slider assembly to provide a desired adjustment of the insulation tube relative to the shaft. A handle assembly is positioned about the housing.

BRIEF DESCRIPTION OF THE DRAWINGS

FIG. 2 is perspective illustration of the FIG. 1 embodiment of the detachable cryosurgical probe shown with the disposable probe assembly detached from the reusable probe assembly.

FIG. 3 is a cross-sectional view of the disposable probe assembly shown attached to the reusable probe assembly, the view being broken away in a few sections to emphasize the showing of the attaching portions of the detachable cryosurgical probe.

FIG. 5 is an enlarged cross-sectional view showing respective attaching portions of the disposable probe assembly and the reusable probe assembly, in an attached configuration.

FIG. 6 is a view taken along line 6-6 of FIG. 5.

FIG. 7 is a view taken along line 7-7 of FIG. 5.

FIG. 8 is an enlarged perspective view of the portion of detachable cryosurgical probe where the detachment takes place.

FIG. 9 shows an initial stage of detachment wherein the breakaway surfaces are detached.

FIG. 10 shows an intermediate stage of detachment showing relative counter rotation of the disposable probe assembly and the reusable probe assembly.

FIG. 11 shows the counter rotation resulting in relative axial motion of the disposable probe assembly and the reusable probe assembly.

FIG. 12 is a perspective view of the breakaway collar of the present invention.

FIG. 13 is a cross-sectional view of the detachable cryosurgical probe just after the breakaway collar has been detached.

FIG. 14 is a cross-sectional view of the detachable cryosurgical probe at the intermediate stage of detachment when the fingers are opening.

FIG. 15 is a cross-sectional view of the detachable cryosurgical probe at the final stage of detachment when the fingers have opened sufficiently to enable the disposable probe assembly to be detached from the reusable probe assembly.

FIG. 16 is a side perspective view of a portion of an alternate embodiment of the detachable cryosurgical probe in which the vacuum tube may be repositioned as desired relative to the shaft, the vacuum tube being in a first position.

FIG. 17 is a front perspective view of the detachable cryosurgical probe of FIG. 16 in the first position and including a showing of the shaft tip.

FIG. 18 shows the detachable cryosurgical probe of FIG. 16 in a second, extended position.

The same elements or parts throughout the figures are designated by the same reference of characters.

DETAILED DESCRIPTION OF THE INVENTION

Figure 1:
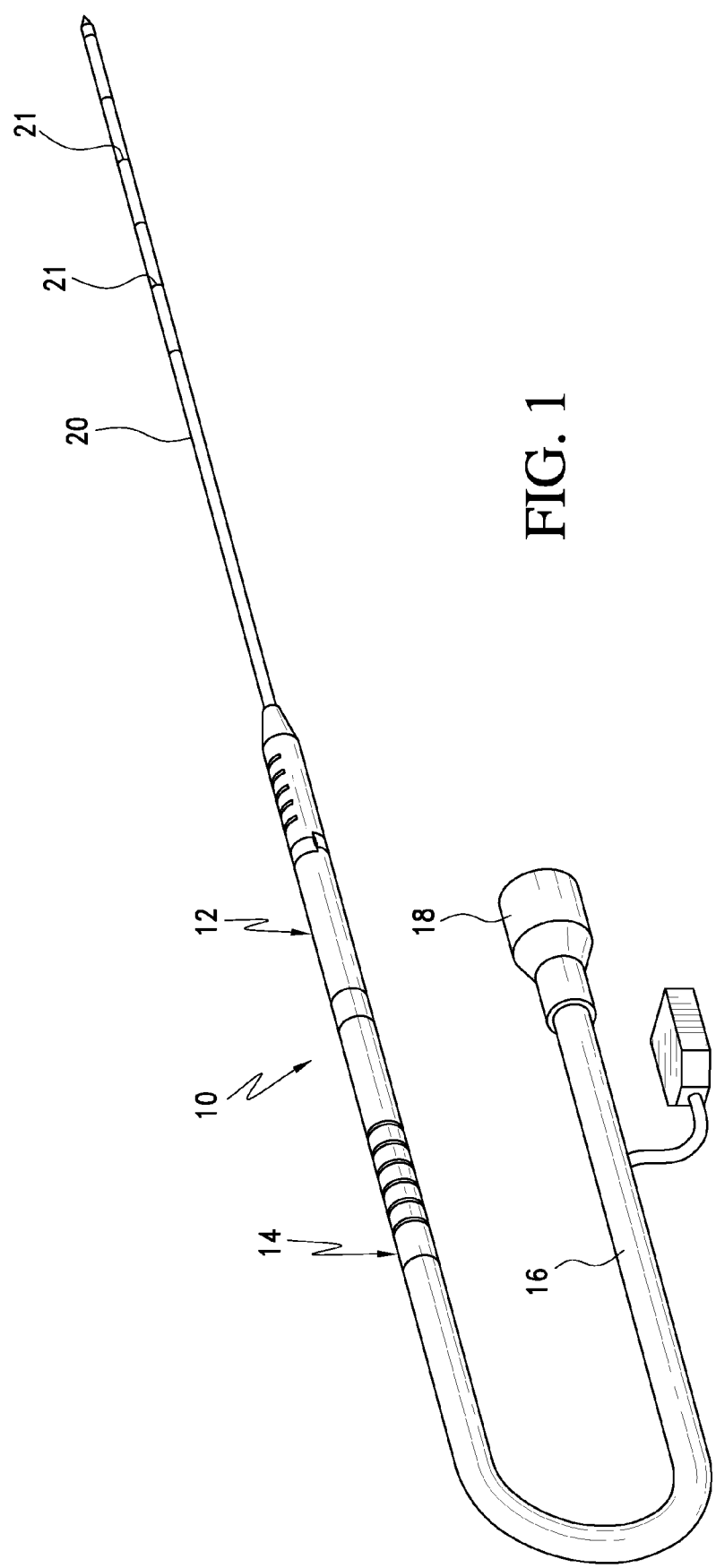
FIG. 1 is a perspective illustration of a first embodiment of the detachable cryosurgical probe with the disposable probe assembly attached to the reusable probe assembly.

Referring now to the drawings and the characters of reference marked thereon, FIG. 1 illustrates a preferred embodiment of the detachable cryosurgical probe of the present invention, designated generally as 10. The detachable cryosurgical probe 10 includes a disposable probe assembly, designated generally as 12 and a reusable probe assembly, designated generally as 14. The reusable probe assembly 14 includes a fluid supply line 16 that is connected at an inlet section 18 to a source (not shown) of cryogenic fluid. The fluid source may be, for example, a cryosurgical system such as that manufactured by present assignee, Endocare, Inc., Irvine, Calif. Such a cryosurgical system typically utilizes argon gas from an argon gas source to provide Joule-Thomson cooling of the cryosurgical probes. Alternatively, nitrogen can be used. Alternatively, a fluid supply system can be utilized that does not require an external fluid supply source. Heating of the cryosurgical probes is typically provided by a helium gas source for providing a helium gas flow through the Joule-Thomson nozzle of the cryosurgical probe. This provides a heating effect. Such heating of the cryosurgical probes is provided to unstick the probes from the treated tissue for cryoprobe removal. A gas delivery assembly of the disposable probe assembly 12 includes a shaft 20 that has a freezing zone. Spaced markings 21 may be provided on the outer surface of the cryosurgical probe 10. These markings 21 may be, for example, at 1 cm intervals.

FIG. 2 shows the disposable probe assembly 12 detached from the reusable probe assembly 14, as will be described in detail below.

Referring now to FIG. 3, the disposable probe assembly 12 is shown attached to the reusable probe assembly 14. This figure is broken away in a few places for the purposes of clarity. The disposable probe assembly 12 includes a gas delivery assembly 22, a finger lock assembly including finger lock element 24, and a disposable handle assembly 26. The gas delivery assembly 22 includes a stem 28 and a fluid conduit subassembly 30 bonded to the stem 28. The fluid conduit subassembly 30 is for delivering and returning cooling fluid used for cryogenic cooling. The finger lock element 24 includes a distal finger lock element section 32 (see also FIG. 6) having a threaded inner surface for engagement with a threaded outer surface of the stem 28. Four radially spaced fingers 34 (see also FIG. 7) extend proximally from the distal finger lock element section 32. Each finger 34 has a ramped surface 36 for operatively engaging an associated ramp section on the stem 28 during use; and, a female lip 38 at a proximal end thereof.

The disposable handle assembly 26 includes a proximal handle section 40, a distal handle section 42; and, a breakaway collar 44. The proximal handle section 40 has a distal end having an inner surface that is operatively engaged with an outer surface of the finger lock element 24 (this region of engagement designated 46) so as to resist relative rotation and axial motion therebetween. As can be seen in FIG. 6, hex shaped surfaces are utilized to prevent relative rotation; however, obviously other geometric shapes and other means can be used to prevent such rotation such as radial bumps, pins, etc.

The distal handle section 42 of the disposable handle assembly 26 has an inner surface that is operatively engaged with another outer surface of the stem 28 (this region of engagement designated 48) so as to resist relative rotation and axial motion therebetween. Again, this region of engagement may be hex shaped. The breakaway collar 44 is positioned between the proximal handle section 40 and the distal handle section 42.

The fluid conduit subassembly 30 includes a Joule-Thomson (J-T) tube 50 bonded to the stem 28. It may be welded thereto, as shown by numeral designation 52. The J-T tube 50 receives the cooling fluid from the reusable probe assembly 14. The distal end of the J-T tube 50 comprises a J-T nozzle 54. A safety washer 56 is positioned within a front end of an elongated central opening 58 of the distal handle section 42 of the disposable handle assembly 26.

A shaft 60 of the fluid conduit subassembly 30 is secured to the safety washer 56 within an opening of the safety washer 56 and within the elongated central opening 58. The shaft 60 extends beyond the distal handle section 42 to provide a cooling surface for cryogenic cooling. In this embodiment a vacuum tube 62 is integrally connected with an inner surface of the shaft 60. (As will be disclosed below in another embodiment there may alternatively be a slideable connection.) A high pressure seal comprising a high pressure o-ring 63 is positioned about a proximal end section of the stem 28 for sealing cooperation (as shown by numeral designation 64 in FIG. 5) with an inner surface of a manifold assembly 66 of the reusable probe assembly 14. The vacuum tube 62 has a desired insulative air gap formed therein. The air gap provides selected non-cooling areas of the cryosurgical probe.

Figure 4:
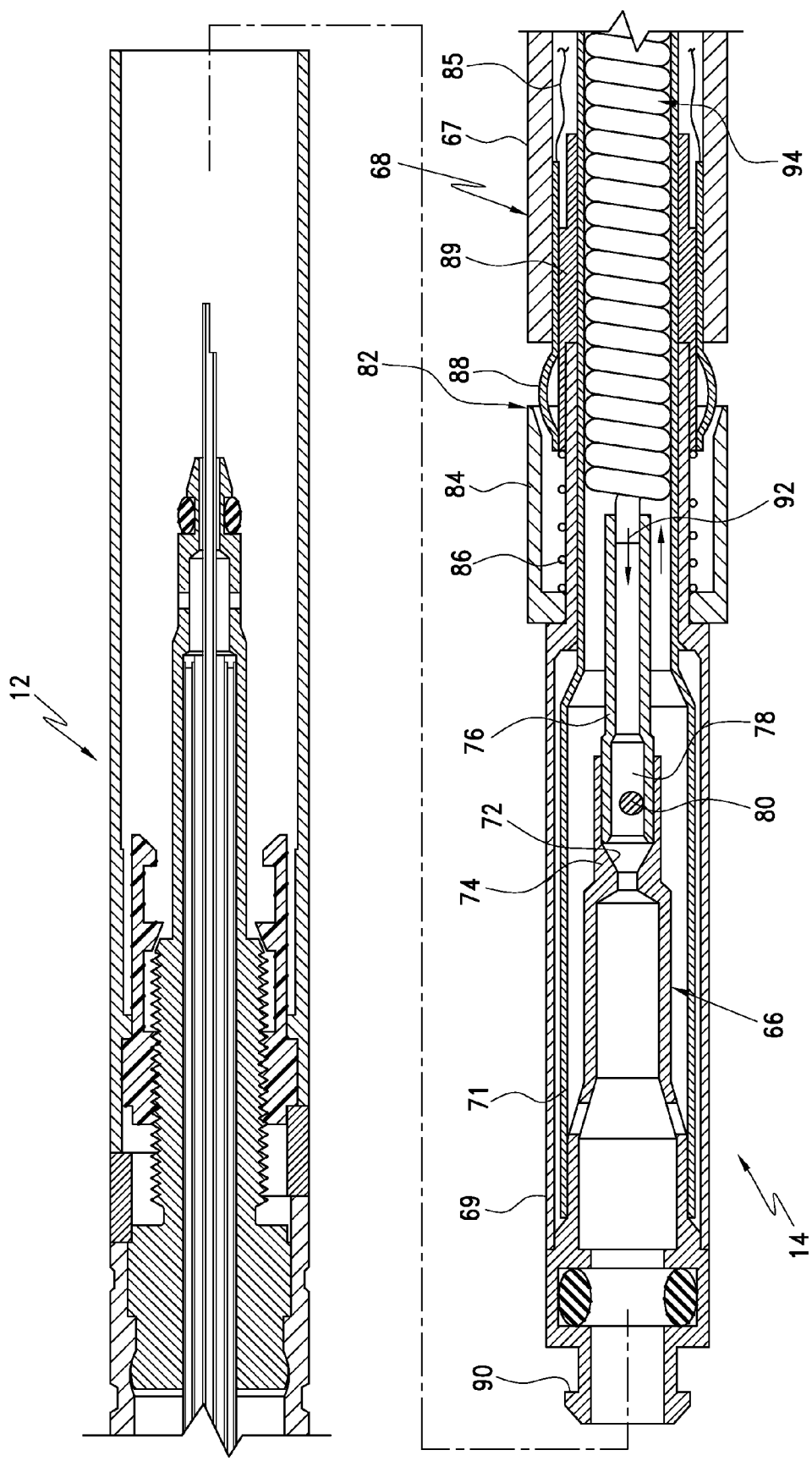
FIG. 4 is a cross-sectional view showing respective attaching portions of the disposable probe assembly and the reusable probe assembly, in a detached configuration.

Referring now to FIG. 4, the reusable probe assembly 14 includes the manifold assembly 66 and a reusable handle assembly 68 secured about the periphery of the manifold assembly 66. The reusable handle assembly 68 includes a first end portion 67 and a second end portion 69. The manifold assembly 66 includes an outer covering 71.

The reusable probe assembly preferably includes a safety valve assembly, designated generally as 70, operatively engaged with the manifold assembly 66 for impeding cryogenic working fluid flow when the disposable probe assembly 12 is detached from the reusable probe assembly 14. The safety valve assembly 70 includes a conical surface 72 formed in a proximal penultimate section 74 of a proximal end portion of the manifold assembly 66. The manifold assembly 66 terminates, at its proximate end, with a proximal ultimate section 76. The proximal ultimate section has a ball retaining cavity 78 formed therein. A ball 80 is positioned within the ball retaining cavity 78. The function of this safety valve assembly 70 will be discussed below in detail.

The reusable probe assembly also preferably includes an electrical confirmation assembly, designated generally as 82, operatively engaged with the disposable probe assembly 12 for providing electrical confirmation that the disposable probe assembly 12 is connected. The electrical confirmation assembly 82 includes a slideable electrically conductive ring 84 positioned about an outer surface of the reusable probe assembly 14 and normally distally biased by a spring 86. The electrical confirmation assembly 82 includes stationary electrically conductive lever spring contact 88 and plastic housing 89 for the lever spring contact 88. The lever spring contact 88 is electrically connected to the cryosurgical system by wires 85. The function of this electrical confirmation assembly 82 will be discussed below in detail.

In operation, when the disposable probe assembly is attached, as can be seen in FIGS. 5, 8, and 12 the breakaway collar 44 is an integral unit that prevents relative rotation between the proximal handle section 40 and the distal handle section 42. In this configuration, the female lip 38 engages a male lip 90 of the manifold assembly 66; thereby securing the reusable probe assembly 12 to the disposable probe assembly 14.

Referring now to FIGS. 9 and 13, during an initial stage of detachment of the disposable probe assembly, the user rotates the distal handle section in a first direction relative to the proximal handle section to "break away" breakaway surfaces of the breakaway collar 44, allowing the breakaway collar 44 to radially expand. In FIG. 13 the breakaway collar 44 is shown removed; however, during actual operation it may possibly dangle at that location.

Referring now to FIGS. 10 and 14, during an intermediate stage of detachment of the disposable probe assembly 12 the user counter rotates the distal handle section 42 in an opposite second direction relative to the proximal handle section 40. The relative rotation between the distal handle section 42 and the proximal handle section 40 provides axial movement of the distal handle section 42 toward the proximal handle section 40 via the engagement of the threaded inner surface of the distal finger lock element section 32 and the threaded outer surface of the stem 30. The axial movement is enabled by the radial expansion of the breakaway collar 44. The ramped surfaces 36 of the radially spaced fingers 34 engage the associated ramp section on the stem 30 during the axial movement thereby urging the fingers 34 to open.

Referring now to FIGS. 11 and 15, during a final stage of detachment, the fingers 34 open sufficiently to allow disengagement of the male lip 90 from the female lip 38, thus enabling the disposable probe assembly 14 to be detached from the reusable probe assembly 12.

As mentioned above, the safety valve assembly 70, is operatively engaged with the manifold assembly 66 for impeding cryogenic working fluid flow when the disposable probe assembly 12 is detached from the reusable probe assembly 14. As can be seen in FIG. 15, when the disposable probe assembly 12 is detached from the reusable probe assembly 14 and no cooling gas is flowing within manifold assembly 66, the ball 80 is free to float freely within the ball retaining cavity 78. However, when the disposable probe assembly 12 is detached from the reusable probe assembly 14 and cooling gas is flowing within the manifold assembly 66 (as indicated by arrow 92), the ball 80 is urged into a volume defined by the conical surface 72, thus providing sufficient sealing to prevent "whipping" of the disposable probe assembly 12. As perhaps best seen in FIG. 5, when the disposable probe assembly 12 is connected to the reusable probe assembly 14 the Joule-Thomson (J-T) tube 50 bonded to the stem 28 maintains the ball 80 in a position away from the conical surface 72, thus allowing the free flow of cooling gas 92 into the disposable probe assembly 12.

As mentioned above, and referring again to FIG. 4, an electrical confirmation assembly, designated generally as 82, is operatively engaged with the disposable probe assembly 12 for providing electrical confirmation that the disposable probe assembly 12 is connected. When the disposable probe assembly 12 is not connected, the conductive ring 84 is not in contact with the lever spring contact 88. When the disposable probe assembly 12 is connected, the conductive ring 84 is urged by the disposable probe assembly 12 in a proximal direction so that it contacts the lever spring contact 88 providing a closed electrical circuit and electrical confirmation of the connection.

A heat exchanger or cryostat 94 is utilized to provide heat exchange between inlet gas and outlet gas. Although, as shown, the heat exchanger is preferably a coiled fin tube heat exchanger various other types of heat exchangers may be utilized such as a tube-in-tube sintered cryostat, threaded cryostat, coiled/sintered cryostat, or stacked coil cryostat. These different types of cryostats are disclosed and claimed in U.S. Ser. No. 10/828,031 (U.S. Pat. No. 7,160,291), entitled Detachable Cryosurgical Probe, filed on Apr. 20, 2004, incorporated herein by reference in its entirety.

Referring now to FIGS. 16-21 a second embodiment of the detachable cryosurgical probe system is illustrated, designated generally as 100. In this system 100 the vacuum tube may be repositioned as desired relative to the shaft. This is accomplished by actuating a button assembly, designated generally as 102, along a guideway 104. FIGS. 16 and 17 show the vacuum tube in a first position (i.e. labeled P5). FIG. 18 shows the vacuum tube moved to a second position (i.e. labeled P2).

Figure 19:
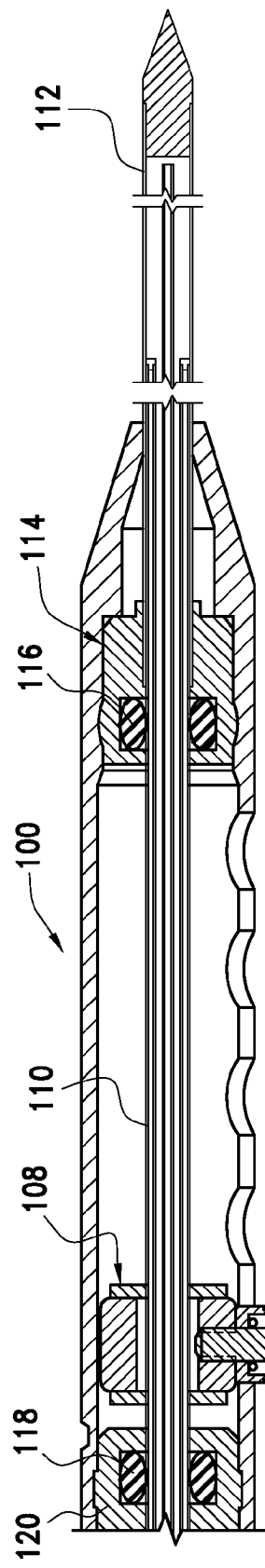
FIG. 19 is a cross-sectional view of the detachable cryosurgical probe of FIG. 16 in the first position.

Referring now to FIG. 19, the button assembly 102 can be seen in cross-section in the first position. A button 104 of the button assembly 102 is biased by a spring 106. A slider assembly 108 is mechanically connected to the vacuum tube 110 and to the button assembly 102. Thus, the shaft 112 and the vacuum tube 110 are capable of moving relative to each other. The button assembly 102 can be locked into position to prevent unintentional movement. A safety washer assembly 114 is securely connected to the shaft 112. It includes an o-ring 116 for sealing the shaft 112 and the vacuum tube 110. Another o-ring 118 at the front of the stem 120 seals the vacuum tube 110 and stem 120.

Figure 20:
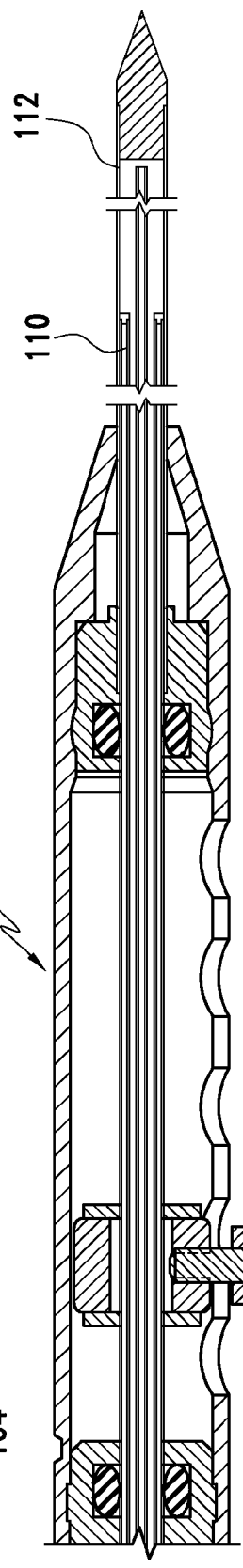
FIG. 20 shows the detachable cryosurgical probe being moved between two positions.
Figure 21:
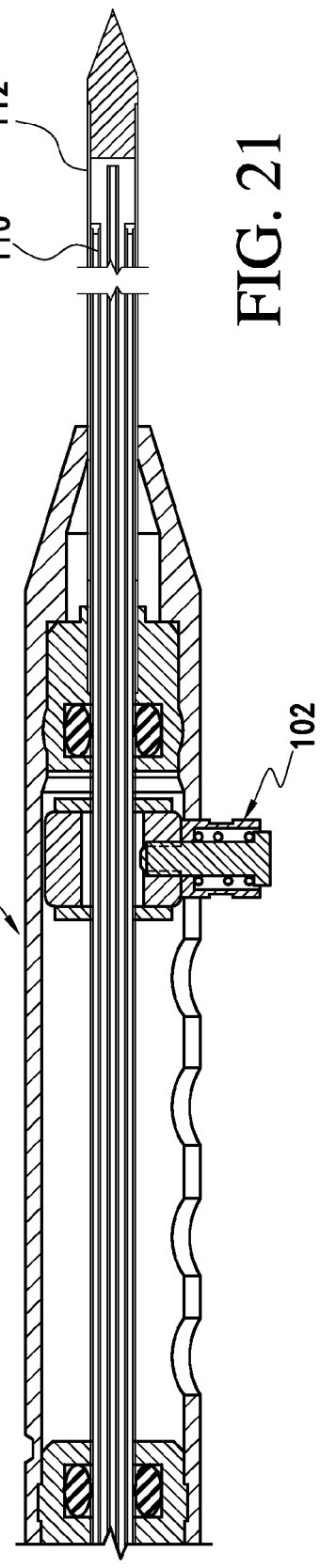
FIG. 21 shows the detachable cryosurgical probe moved to a second position.

Referring now to FIG. 20, the vacuum tube 110 is shown having been moved toward a second position relative to the shaft 112 by the actuation of button assembly 102. Referring now to FIG. 21, the button assembly 102 is shown moved to position P4. Thus, the size and shape of the generated iceball can be varied in accordance with a specific desired need.

The slider assembly 108 and button assembly 102 are collectively an adjustable sliding apparatus. The vacuum tube 110 serves as an insulation element.

During operation, with the disposable probe assembly 12 attached to the reusable probe assembly 14, cryogenic fluid originating from (typically) an argon tank flows through the supply line 16 within the cryostat 94 and through the manifold assembly as shown by arrow 92 (in, for example, FIG. 5). The flow is directed through the safety valve assembly 70 and then through the central passageway in the high pressure stem 28 via J-T tube 50, and out of the J-T port 54 (see FIG. 3).

After being expelled from the J-T port 54 the return fluid is directed in the space between the inner surface of the vacuum tube 62 and the outer surface of the J-T tube 50. It then flows through openings in the manifold assembly 66, as indicated by arrow 114 (FIG. 5) and adjacent to the heat exchanger 94. The return fluid is eventually expelled via the hose 16.

In the device illustrated the cryosurgical probe is shown with a pointed tip to provide insertion into the patient's tissue for the desired application. However, it is understood that the tip may be blunt, depending on the application. For example, for certain applications direct insertion is desirable. For other applications, insertion via a cannula/introducer is preferred.

Although application of this device utilizing CT guidance is preferred, the cryosurgical probe 10 may be used with a variety of guidance tools, such as MRI and ultrasound. In one preferred implementation ultrasound is used for initial guidance, followed up with CT for final confirmation.

Although the present invention has been discussed above with respect to a cryosurgical probe having a rigid outer sheath, the cryosurgical probe may be made to be malleable by including at least one malleable segment thereon. Malleable segments are formed of material that permit reshaping and bending to reposition the ablating surface for greater ablation precision. An example of a cryosurgical probe having malleable characteristics is disclosed and claimed in our co-pending patent application Ser. No. 09/957,337, Pub. No. US 2003/0055415 A1, filed on Sep. 20, 2001 (U.S. Pat. No. 6,936,045) entitled Malleable Cryosurgical Probe, incorporated in its entirety herein by reference.

One method for providing malleable characteristics includes providing a malleable shaft with a bellows portion. U.S. Pat. No. 6,767,346, filed on Jul. 27, 2002 entitled Cryosurgical Probe With Bellows Shaft, incorporated in its entirety herein by reference, discloses use of a bellows portion for providing the necessary reshaping and bending.

If the detachable cryosurgical probe is utlilized in combination with ultrasound the outer sheath may have an echogenic coating with, for example, a porous microstructure having the ability to trap microscopic air bubbles. This creates thousands of highly efficient ultrasound reflectors on the surface of the sheath.

Thus, while the preferred embodiments of the devices and methods have been described in reference to the environment in which they were developed, they are merely illustrative of the principles of the invention.

For example, even though the finger lock element has been described specifically with respect to the present cryosurgical probe it is understood that it can be used on other types of cryosurgical probes that, for example, may not be single use. Further, the finger lock element may be used for many applications which require a quick disconnect (both single use and multiple use). These may include, for example, control valves for water heaters, pneumatic systems for controls that require quick disconnects, electrical connectors, etc.

Although the cryostat 94 has been shown positioned within the manifold assembly 66 it may be positioned in other locations, notably, for example, in the hose 16 or within the fluid source.

Although the cryosurgical probe system is particularly advantageous for prostate cryosurgery it is also advantageous for many other types of ablation applications, such as radiological applications.

Other embodiments and configurations may be devised without departing from the spirit of the invention and the scope of the appended claims.

The invention claimed is:

1. A cryosurgical probe assembly, comprising:
   a) a gas delivery assembly, comprising a stem and a fluid conduit subassembly bonded to said stem, said fluid conduit subassembly for delivering and returning cooling fluid used for cryogenic cooling, said fluid conduit subassembly, comprising:
      i. a shaft for providing a heat exchange surface for cryogenic ablation;
      ii. a housing securely connected to said shaft; and,
      iii. an insulation element slideably engaged with an inner surface of said shaft and slideably engaged with said stem;
   b) an adjustable sliding apparatus, comprising:
      i. a slider assembly securely attached to said insulation element for slideably guiding said insulation element along said shaft; and,
      ii. a button assembly operatively connected to said slider assembly for allowing a user to actuate said slider assembly to provide a desired adjustment of said insulation element relative to said shaft; and,
   c) a handle assembly positioned about said housing.

2. The cryosurgical probe assembly of claim 1, wherein said insulation element comprises a vacuum tube.

3. The cryosurgical probe assembly of claim 1, wherein said cryosurgical probe assembly is detachable.

4. The cryosurgical probe system of claim 1, wherein said handle comprises a guideway formed therein for providing access to said button assembly.

5. The cryosurgical probe system of claim 1, wherein said button assembly can be locked into position to prevent unintentional movement.

6. The cryosurgical probe assembly of claim 1, wherein said cryosurgical probe assembly is a disposable probe assembly of a detachable cryosurgical probe, said disposable probe assembly, further comprising:
   a) a finger lock element, comprising:
      1. a distal finger lock element section having a threaded inner surface for engagement with a threaded outer surface of said stem; and,
      2. a plurality of radially spaced fingers extending proximally from said distal finger lock element section, each finger having a) a ramped surface for operatively engaging an associated ramp section on said stem during use; and, b) a female lip at a proximal end thereof.

7. The cryosurgical probe system of claim 1, wherein said gas delivery system includes a Joule-Thomson (J-T) tube bonded to said stem.

8. The cryosurgical probe system of claim 1, wherein said fluid conduit subassembly, comprises:
   a) a Joule-Thomson (J-T) tube bonded to said stem, said J-T tube for receiving cooling fluid from a reusable probe assembly;
   b) a safety washer positioned within a front end of an elongated central opening of said distal handle section of said handle assembly;
   c) a shaft secured to said safety washer within an opening of said safety washer and within said elongated central opening, said shaft extending beyond a distal handle section of said handle assembly to provide a cooling surface for cryogenic cooling;
   d) said vacuum tube integrally connected to an inner surface of said shaft; and,
   e) a high pressure seal comprising a high pressure o-ring positioned about a proximal end section of said stem, for sealing cooperation with an inner surface of a manifold assembly of the reusable probe assembly.

9. The cryosurgical probe system of claim 1, wherein said fluid conduit subassembly, comprises:
   a) a Joule-Thomson (J-T) tube bonded to said stem, said J-T tube for receiving cooling fluid from a reusable probe assembly;
   b) a safety washer assembly positioned within a front end of an elongated central opening of a distal handle section of said handle assembly, said safety washer assembly including a first o-ring,
      i. said shaft being secured to said safety washer assembly within an opening of said safety washer and within said elongated central opening, said shaft extending beyond said distal handle section to provide a cooling surface for cryogenic cooling,
      ii. said first o-ring for sealing said shaft to said vacuum tube; and,
   c) a second o-ring positioned within a front end of said stem, for sealing cooperation with said vacuum tube.

* * * * *

UNITED STATES PATENT AND TRADEMARK OFFICE
CERTIFICATE OF CORRECTION

PATENT NO. : 7,608,071 B2
APPLICATION NO. : 11/857095
DATED : October 27, 2009
INVENTOR(S) : Thach Duong et al.

It is certified that error appears in the above-identified patent and that said Letters Patent is hereby corrected as shown below:

On the title page, in the heading Related U.S. Application Data,

Please delete (63) in its entirety and insert therefor:

-- (63) Continuation of application No. 11/685,058, filed on Mar. 12, 2007, now Pat. No. 7,381,207, which is a continuation-in-part of application No. 11/116,873, filed on Apr. 28, 2005, now Pat. No. 7,189,228, which is a continuation-in-part of application No. 10/603,883, filed on Jun. 25, 2003, now Pat. No. 7,207,985. --

In Column 1, lines 9-10, please delete "filed on Mar. 12, 2007, which is a continuation of U.S. Ser. No. 11/116,873" and insert therefor -- filed on Mar. 12, 2007, which is a continuation-in-part of U.S. Ser. No. 11/116,873 --

Signed and Sealed this
Twenty-second Day of January, 2013

David J. Kappos
*Director of the United States Patent and Trademark Office*